(12) United States Patent
Arroyo et al.

(10) Patent No.: US 7,482,156 B2
(45) Date of Patent: Jan. 27, 2009

(54) HEPATOCELLULAR CARCINOMA SPECIFIC PROMOTER AND USES THEREOF

(75) Inventors: Trini Arroyo, Palo Alto, CA (US); Yuanhao Li, Palo Alto, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 10/947,812

(22) Filed: Sep. 22, 2004

(65) Prior Publication Data

US 2005/0124068 A1 Jun. 9, 2005

Related U.S. Application Data

(60) Provisional application No. 60/511,812, filed on Oct. 15, 2003.

(51) Int. Cl.
*C12N 5/16* (2006.01)
*C12N 15/861* (2006.01)

(52) U.S. Cl. .................................... 435/325; 435/320.1
(58) Field of Classification Search ....................... None
See application file for complete search history.

(56) References Cited

U.S. PATENT DOCUMENTS

| | | | |
|---|---|---|---|
| 5,677,178 | A | 10/1997 | McCormick |
| 5,698,443 | A | 12/1997 | Henderson |
| 5,770,442 | A | 6/1998 | Wickham |
| 5,801,029 | A | 9/1998 | McCormick |
| 5,830,686 | A | 11/1998 | Henderson |
| 5,955,273 | A | 9/1999 | Hochberg |
| 5,994,128 | A | 11/1999 | Fallaux |
| 5,998,205 | A | 12/1999 | Hallenbeck |
| 6,306,833 | B1 | 10/2001 | Hochberg |
| 6,432,700 | B1 | 8/2002 | Henderson |
| 6,436,394 | B1 | 8/2002 | Henderson |
| 6,495,130 | B1 | 12/2002 | Henderson |
| 6,551,587 | B2 | 4/2003 | Hallenbeck |
| 6,585,968 | B2 | 7/2003 | Little |
| 6,638,762 | B1 | 10/2003 | Chang |
| 6,676,935 | B2 | 1/2004 | Henderson |
| 6,692,736 | B2 | 2/2004 | Yu |
| 2001/0053352 | A1 | 12/2001 | Yu |
| 2002/0115094 | A1 | 8/2002 | Farnham et al. |
| 2002/0120117 | A1 | 8/2002 | Zhang |
| 2002/0136707 | A1 | 9/2002 | Yu |
| 2002/0192187 | A1 | 12/2002 | McClelland |
| 2003/0026792 | A1 | 2/2003 | Lamparsky |
| 2003/0039633 | A1 | 2/2003 | Yu |
| 2003/0068307 | A1 | 4/2003 | Yu |
| 2003/0104625 | A1 | 6/2003 | Cheng |
| 2003/0148520 | A1 | 8/2003 | Yu et al. |
| 2003/0152553 | A1 | 8/2003 | Henderson |
| 2005/0074762 | A1 * | 4/2005 | Nakamura et al. ............. 435/6 |

FOREIGN PATENT DOCUMENTS

| | | |
|---|---|---|
| WO | WO 92/03563 | 3/1992 |
| WO | WO 95/19434 | 7/1995 |
| WO | WO 96/17053 | 6/1996 |
| WO | WO 98/13499 | 4/1998 |
| WO | WO 98/39464 | 9/1998 |
| WO | WO 98/39465 | 9/1998 |
| WO | WO 98/39466 | 9/1998 |
| WO | WO 98/39467 | 9/1998 |
| WO | WO 99/06576 | 2/1999 |
| WO | WO 99/25860 | 5/1999 |
| WO | WO 00/15820 | 3/2000 |
| WO | WO 01/73093 | 10/2001 |
| WO | WO 01/73093 A2 | 10/2001 |
| WO | WO 03/007859 | 1/2003 |
| WO | WO 03/104476 | 12/2003 |
| WO | WO 2004/042025 | 5/2004 |

OTHER PUBLICATIONS

Rowen et al., "*Homo sapiens* chromosome 15 clone RP11-108K3M3 map 15q21" Database GenEmbl, AC20891, "Sequencing of human chromosome 15 D15S146-D15S117 region", available Jan. 30, 2001, sequence result file.*
Blackwood et al., Going the Distance: A Current View of Enhancer Action, Science, 1998, 281:60-63.
Brannon et al., The Product of the H19 Gene May Function As An RNA, 1990, Molecular and Cellular Biology, 10(1): 28-36.
Doronin et al., Tumor-Specific, Replication-Competent Adenovirus Vectors Overexpressing the Adenovirus Death Protein, Journal of Virology, 2000, 74(13):6147-6155.

(Continued)

*Primary Examiner*—Nancy Vogel
(74) *Attorney, Agent, or Firm*—Ropes & Gray LLP; James F. Haley, Jr.; Teresa Chen

(57) ABSTRACT

Liver cancer, particularly hepatocellular carcinoma specific promoter sequences and adenovirus vehicles are provided. By providing for transcriptional initiating regulation dependent upon transcription factors that are only active in specific, limited cell types, virus replication will be restricted to the target cells. The modified adenovirus may be used as a vehicle for introducing new genetic capability, particularly associated with cytotoxicity, for treating neoplasia.

11 Claims, 4 Drawing Sheets

OTHER PUBLICATIONS

Doronin et al., Tissue-Specific, Tumor-Selective, Replication-Competent Adenovirus Vector for Cancer Gene Therapy, Journal of Virology, 2001, 75(7):3314-3324.

Doronin et al., Overexpression of the ADP (E3-11.6K) Protein Increases Cell Lysis and Spread of Adenovirus, Virology, 2003, 305(2):378-87.

Graveel et al., Identification and Characterization of CRG-L2, A New Marker for Liver Tumor Development, 2003, Oncogene, 22:1730-1736.

Habib et al., E1B-Deleted Adenovirus (d/1520) Gene Therapy for Patients With Primary and Secondary Liver Tumors, Human Gene Therapy, 2001, 12:219-226.

Jakubczak et al., Construction and Characterization of Oncolytic Adenoviruses, Molecular Therapy, 2001, 3(5):Abstract 442.

Kruyt et al., Toward a New Generation of Conditionally Replicating Adenoviruses: Pairing Tumor Selectivity With Maximal Oncolysis, Human Gene Therapy, 2002, 13(4):485-495.

Kwong et al., Combination Therapy With Suicide and Cytokine Genes for Hepatic Metastases of Lung Cancer, Chest, 1997, 112(5):1332-1337.

Nemunaitis et al., Selective Replication and Oncolysis in p53 Mutant Tumors With Onyx-015, An E1B-55Kd Gene-Deleted Adenovirus, in Patients With Advanced Head and Neck Cancer: A Phase II Trial, Cancer Research, 2000, 60:6359-6366.

Russell, Update on Adenovirus and its Vectors, Journal of General Virology, 2000, 81:2573-2604.

Sauthoff et al., Deletion of the Adenoviral E1b-19Kd Gene Enhances Tumor Cell Killing of a Replication Adenoviral Vector, Human Gene Therapy, 2000, 11:379-388.

Smith et al., Transcriptional Regulation of Mammalian Genes in Vivo, 1997, J. Biol. Chem. 272:27493-27496.

Steinwaerder et al., Insulation From Viral Transcriptional Regulatory Elements Improves Inducible Transgene Expression From Adenovirus Vectors in Vitro and in Vuvvo, Gene Therapy, 2000, 7(7):556-567.

Yu et al., Selectively Replicating Oncolytic Adenoviruses as Cancer Therapeutics, Current Opinion in Molecular Therapeutics, 2002, 4(5), pp. 435-443.

Behringer, et al., "Dwarf mice produced by genetic ablation of growth hormone-expressing cells", Genes & Development, vol. 2, pp. 453-461, 1988.

Berkner, et al., "Generation of adenovirus by transfection of plasmids", Nucleic Acids Research, vol. 11, No. 17, pp. 6003-6020, 1983.

Bett, et al., "An efficient and flexible system for construction of adenovirus vectors with insertions or deletions in early regions 1 and 3", Proc. Natl. Acad. Sci. USA, vol. 91, pp. 8802-8806, 1994.

Bett, et al., "Packaging Capacity and Stability of Human Adenovirus Type 5 Vectors", Journal of Virology, vol. 67, No. 10, pp. 5911-5921, 1993.

Bitter, et al., "Expression and Secretion Vectors for Yeast", Methods of Enzymology, vol. 153, pp. 516-544, 1987.

Bridge, et al., "Redundant Control of Adenovirus Late Gene Expression by Early Region 4", Journal of Virology, vol. 63, No. 2, pp. 631-638, 1989.

Duke, et al., "Sequence and Structural Elements That Contribute to Efficient Encephalomyocarditis Virus RNA Translation", Journal of Virology, vol. 66, No. 3, pp. 1602-1609, 1992.

Felgner, et al., "Cationic liposome-mediated transfection", Nature, vol. 337, pp. 387-388, 1989.

Graham, "Covalently closed circles of human adenovirus DNA are infectious", The EMBO Journal, vol. 3, No. 12, pp. 2917-2922, 1984.

Huez, et al., "Two Independent Internal Ribosome Entry Sites Are Involved in Translation Initiation of Vascular Endothelial Growth Factor mRNA", Molecular and Cellular Biology, vol. 18, No. 11, pp. 6178-6190, 1998.

Jackson, et al., "The Animal Picornavirus", Trends in Biochemical Sciences, vol. 15, No. 12, pp. 477-483, 1990.

Jackson, et al., "Internal initiation of translation in eukaryotes: The picornavirus paridigm and beyond", RNA, vol. 1, No. 10, pp. 985-1000, 1995.

Lamb, et al., "Nucleotide sequence of cloned cDNA coding for preproricin", European Journal of Biochemistry, vol. 148, No. 2, pp. 265-270, 1985.

Logan, et al., "Adenovirus tripartite leader sequence enhances translation of mRNAs late after infection", Proc. Natl. Acad. Sci. USA, vol. 81, pp. 3655-3659, 1984.

Maxwell, et al., "Cloning, Sequence Determination, and Expression in Transfected Cells of the Coding Sequence for the tox 176 Attenuated Diphtheria Toxin A Chain", Molecular and Cellular Biology, pp. 1576-1579, 1987.

McKinnon, et al., "Tn5 mutagenesis of the transforming genes of human adenovirus type 5", Gene, vol. 19, pp. 33-42, 1982.

Messing, et al., "$P_o$ Promoter Directs Expression of Reporter and Toxin Genes to Schwann Cells of Transgenic Mice", Neuron, vol. 8, pp. 507-520, 1992.

Piatak, et al., "Expression of Soluble and Fully Functional Ricin A Chain in *Escherichia coli* Is Temperature-sensitive", The Journal of Biological Chemistry, vol. 263, No. 10, pp. 4837-4843, 1988.

Palmiter, et al., "Cell Lineage Ablation in Transgenic Mice by Cell-Specific Expression of a Toxin Gene", Cell, vol. 50, pp. 435-443, 1987.

Rao, et al., "The adenovirus E1A proteins induce apoptosis, which is inhibited by the E1B 19-kDa and Bcl-2 proteins", Proc. Natl. Acad. Sci. USA, vol. 89, pp. 7742-7746, 1992.

Swaminathan, et al. "Regulation of Adenovirus E2 Transcription Unit", Current Topics in Microbiology and Immunology, vol. 199, pp. 17-194, 1995.

Weinberg, et al., "A cell line that supports the growth of a defective early region 4 deletion mutant of human adenvirus type 2", Proc. Natl. Acad. Sci. USA, vol. 80, pp. 5383-5386, 1983.

Wold, et al., "E3 Transcription Unit of Adenovirus", Current Topics in Microbiology and Immunology, vol. 199, pp. 237-274, 1995.

Yu, et al., "Methylation profiling of twenty promoter-CpG islands of genes which may contribute to hepatocellular carinogenesis", BMC Cancer, vol. 2, No. 29, pp. 1-14, 2002.

Supplementary European search report for application No. 04789038.9.

Birren, B. et al., "*Homo sapiens* chromosome 15 clone RP11-129M3 map 15, Working Draft Sequence, 15 unordered pieces", Database Genebank, database accession No. AC021238, see nucleotides 69322-70124, abstract.

Kim, J.W. et al., "Gene expression profiling of preneoplastic liver disease and liver cancer: a new era for improved early detection and treatment of these deadly diseases?", *Carcinogenesis*, Mar. 2003, 24(3):363-369.

Zhao, T. et al.. "Adenovirus with insertion-mutated E1A selectively propagates in liver cancer cells and destroys tumors in Vivo", *Cancer Research*, Jun. 15, 2003, 63(12):3073-3078.

Birren et al., "*Homo sapiens* chromosome 15 clone RP11-129M3 map 15, Working Draft Sequence, 15 unordered pieces", Database Genbank, AC021238, (Jan. 16, 2000).

Kim Jin Woo et al., "Gene expression profiling of preneoplastic liver disease and liver cancer: A new era for improved early detection and treatment of these deadly diseases?", Carcinogenesis (Oxford), vol. 24, No. 3, pp. 363-369 (Mar. 2003).

Zhao Tiejun et al., "Adenovirus with insertion-mutated E1A selectively propagates in liver cancer cells and destroys tumors in vivo", Cancer Research, vol. 63, No. 12, pp. 3073-3078 (Jun. 15, 2003).

* cited by examiner

| | |
|---|---|
| ACCTCCCATGGACAGTGGGCACGTGCCTTAGCATCTGGGCATGCTGATCTTTTTCTCCAA | 60 |
| GAGGGCAGTGTGGGGGTAGAAGGGGGTGGAATCCGGAGACTTCTCTCCATAAGAATTCCT | 120 |
| GCTCTCCCCCTCAGTCTGACCCTTGCTTTGCCTGTCTGGGCCACGGCAATGCCCTCAGGC | 180 |
| AGAGCAGTGGGAAGAGGAGGAGAGGGTTTGCTCAGCTGGCGGGACTCTGGGAGCACGAGC | 240 |
| CCTGCCAGCCCCTCCTCCGCAGGCTGCCTCCACTGGCTCCTCTCCTGCTTCTGCCCGCCT | 300 |
| GTCCCTCTGGGCTGCTCGGGCGCCACCACTACTGTCCCCATCCCGCCCCGCCAGCTGGGC | 360 |
| CAAAGGGTGACTTGACTCACGACGCTGCCACCAGCCCACGGCTTGCCCGAGGCGTATAAA | 420 |
| GGCTGCCAGGGCCGCAGGCTGCCAAGCCCTGCCCTGCCCAAGGCGCATAGAGCATGGCCC | 480 |
| GAGGCGCTGAGGGAGGCCGTGGGGACGCGGGTTGGGGCCTGCGTGGCGCCCTGGCGGCCG | 540 |
| TGGCGCTGCTCTCGGCGCTCAACGCTGCGGGCACGGTGTTCGCGCTGTGCCAGTGGCGCG | 600 |
| GGCTGAGCTCGGCGCTGCGGGCTTTGGAGGCGCAGCGGGGCCGGGAGCAGCGCGAGGACA | 660 |
| GTGCCCTGCGCTCCTTCCTGGCCGAGTTGAGCCGCGCGCCGCGCGGGGCGTCCGCACCAC | 720 |
| CCCAAGACCCGGCCAGCTCAGCTCGCAACAAGCGCAGCCACAGCGGCGAGCCCGCGCCGC | 780 |
| ATATCCGCGCCGAGAGCCATGAC | 803 |

Figure 1

HEPATOCELLULAR CARCINOMA SPECIFIC PROMOTER AND USES THEREOF

BACKGROUND OF THE INVENTION

Cancer of the liver is a rare malignancy in the United States, but in parts of Asia and Africa, it is one of the most common malignancies. The areas of highest incidence are in eastern Asia and sub-Saharan Africa, and HCC can be the dominant cause of cancer mortality in these areas. Although incidence is very low in Western countries, ethnic subgroups in these populations may be at very high risk due to the high prevalence of chronic hepatitis B virus (HBV) infection. Because survival times for patients with HCC are short, incidence and mortality figures are roughly equivalent. In the United States, 5-year survival rates for liver cancers over the past two decades remain at about 5%.

The epidemiologic association of chronic HBV or HCV infection with hepatocellular carcinoma has been well established. For patients with chronic viral hepatitis, screening for early-stage hepatocellular carcinoma may permit the institution of curative treatment strategies, and antiviral treatment may reduce the risk of subsequent development of hepatocellular carcinoma. For patients with established hepatocellular carcinoma, the presence of concurrent chronic viral hepatitis or cirrhosis may affect prognosis and survival and may alter treatment options because of impaired hepatic function.

Incidence of hepatocellular carcinoma increases with age, with the age of peak incidence varying somewhat with population. HCC is seen in childhood in areas where HBV is endemic and infection occurs primarily at birth or early childhood. In all populations worldwide, there is a strong male predominance in HCC incidence. Several possible explanations for this have been proposed, including higher rates of HBV carriage among males, genetic susceptibility, androgenic steroids, higher body iron stores, and higher exposure to other hepatocarcinogenic cofactors (e.g., alcohol, aflatoxin).

Familial aggregation of HCC has been reported, primarily in families where chronic HBV infection is also present. Some studies, however, have found an effect of family history independent of HBV status. Familial aggregation may be explained by the interaction of HBV and a major gene. Familial aggregation has also been reported for hepatoblastoma, which occurs in families carrying germline mutations of the APC (adenomatous polyposis coli) gene.

Because of the high prevalence of HBV infection in certain regions of China, a screening program for hepatocellular carcinoma was instituted for adults over the age of 35 with chronic HBV infection. The screening tests used were serum alpha-fetoprotein (AFP) and liver ultrasonography performed every 6 months. The AFP has a sensitivity of 70%, since up to 30% of hepatocellular carcinomas do not secrete it. Liver ultrasonography has up to 70% sensitivity for the detection of HCCs that are less than 2 cm, but has poor specificity. The combination of AFP and ultrasonography, however, increases both sensitivity and specificity.

The prognosis for liver carcinoma patients is poor. Patients with metastatic or locally advanced HCC usually respond poorly to anticancer treatments. Untreated patients usually die in 3-4 months; treated patients may live 6 to 18 months if they respond to therapy. Long-term survival is seen occasionally after successful subtotal hepatectomy for noninvasive carcinoma. Because the normal metabolic and storage functions of the liver are impaired, patients are at risk for nutritional and bleeding complications. Patients with advanced cirrhosis commonly succumb to complications such as encephalopathy, variceal hemorrhage, and sepsis, independently of the tumor's extent.

Treatment decisions are also based on the presence of active hepatitis or cirrhosis. Doxorubicin, the most active chemotherapy agent for HCC, is metabolized and excreted by the liver. The pharmacokinetics for doxorubicin may be changed for patients with liver dysfunction, resulting in enhanced toxicity. Hepatic resection, a treatment of choice for solitary HCC, can result in hepatic failure if hepatic reserve is compromised by hepatitis or cirrhosis. For patients with unresectable HCC, orthotopic liver transplantations have produced prolonged survival. Patients with stage I or II HCC have 5-year survivals following transplantation that are comparable to those of patients transplanted for cirrhosis without HCC. This survival advantage is attenuated, however, in patients with active HBV viral replication (HBeAg or high levels of HBV DNA) because of the high incidence of severe viral re-infections of the liver allograft. Although patients with HCV infection also have a high incidence of re-infection following transplantation, the disease is indolent and eventual cirrhosis may not occur for decades.

Several viruses have recently come forth as both vehicles for gene therapy and as candidate anticancer agents. Among them adenovirus, a mildly pathogenic human virus that propagates prolifically in epithelial cells, the origin of many human cancers. Adenovirus has emerged as a virus that can be engineered with oncotropic properties. See, for example, U.S. Pat. No. 5,846,945 (Onyx); U.S. Pat. No. 5,801,029 (Onyx); U.S. Pat. No. 5,747,469 (Univ Texas); PCTUS1999/08592 (WO 99/59604; Onyx) or PCT/US1998/03514 (WO 98/35554; Canji); PCT/US1997/22036 (WO 98/29555; Onyx). Replication competent adenovirus vectors have been designed to selectively replicate in tumor cells. Improving the delivery of these adenoviruses, both to local-regional and disseminated disease, as well as improving the virus to promote intratumoral spread are of particular interest.

Several experimental cancer therapies utilize various aspects of adenovirus or adenovirus vectors. See, for example, U.S. Pat. Nos. 5,846,945; 5,801,029; PCT/US99/08592; U.S. Pat. No. 5,747,469; PCT/US98/03514; and PCT/US97/22036.

Although replication competent adenoviruses may be able to achieve selective targeting and amplification for the treatment of local and disseminated cancer, there remains a need for improvement in both the adenovirus vectors themselves and methods for their use. Preliminary results suggest that the features of effective treatment strategies for various types of cancer may require development of specific adenovirus vectors and/or methods particular to the type of cancer under treatment. Although chemotherapy and immunotherapy are the most prevalent current therapeutic strategies for disseminated tumors, both toxic side effects and lack of efficacy remain a problem.

There is, therefore, substantial interest in development of viral vectors which enable the targeting of specific cancers in vivo.

SUMMARY OF THE INVENTION

The present invention provides replication-competent adenoviral vectors comprising a liver cancer-specific transcriptional regulatory element (TRE) operably linked to a gene required for virus replication.

In one aspect of the invention, genetic sequences comprising liver cancer specific TREs derived from the CRG-L2 gene are provided. The hepatocellular carcinoma specific TRE may be derived from the 0.8 kb sequence upstream of the translational start codon for the CRG-L2 gene, presented herein as SEQ ID NO:1, or from a 0.7 kb sequence contained within SEQ ID NO:1 (residues 119-803); or as an EcoRI to NcoI fragment derived from the 0.8 kb sequence.

In one embodiment of the invention, a vector comprising the CRG-L2 promoter is provided. The vector may comprise a coding sequence operably linked to the CRG-L2 promoter. Vectors of interest include plasmids, viral vectors, genome integrating vectors, and the like. Viral vectors of interest include adenoviral vectors.

Adenoviral vectors of the invention may comprise one or more liver cancer-specific TREs, and may further comprise one or more regulatory sequences, e.g. enhancers, promoters, transcription factor binding sites and the like, which may be derived from the same or different genes.

The adenovirus vectors may comprise co-transcribed first and second adenoviral genes under control of a liver cancer-specific TRE and the second gene may be under translational control of an internal ribosome entry site (IRES). Methods are provided for introducing into a cell an adenoviral vector comprising a liver cancer-specific TRE operably linked to a gene required for virus replication, and host cells comprising the adenovirus vector(s). In another aspect, methods are provided for conferring selective cytotoxicity in target primary liver cancer cells, particularly hepatocellular carcinoma cells, comprising contacting the cells with an adenovirus vector of the invention, whereby the vector enters the cell and propagates virus.

BRIEF DESCRIPTION OF THE DRAWINGS

FIG. 1. Sequence of CRG-L2 0.8 Kb TRE DNA.

DETAILED DESCRIPTION OF THE EMBODIMENTS

Figure 2:
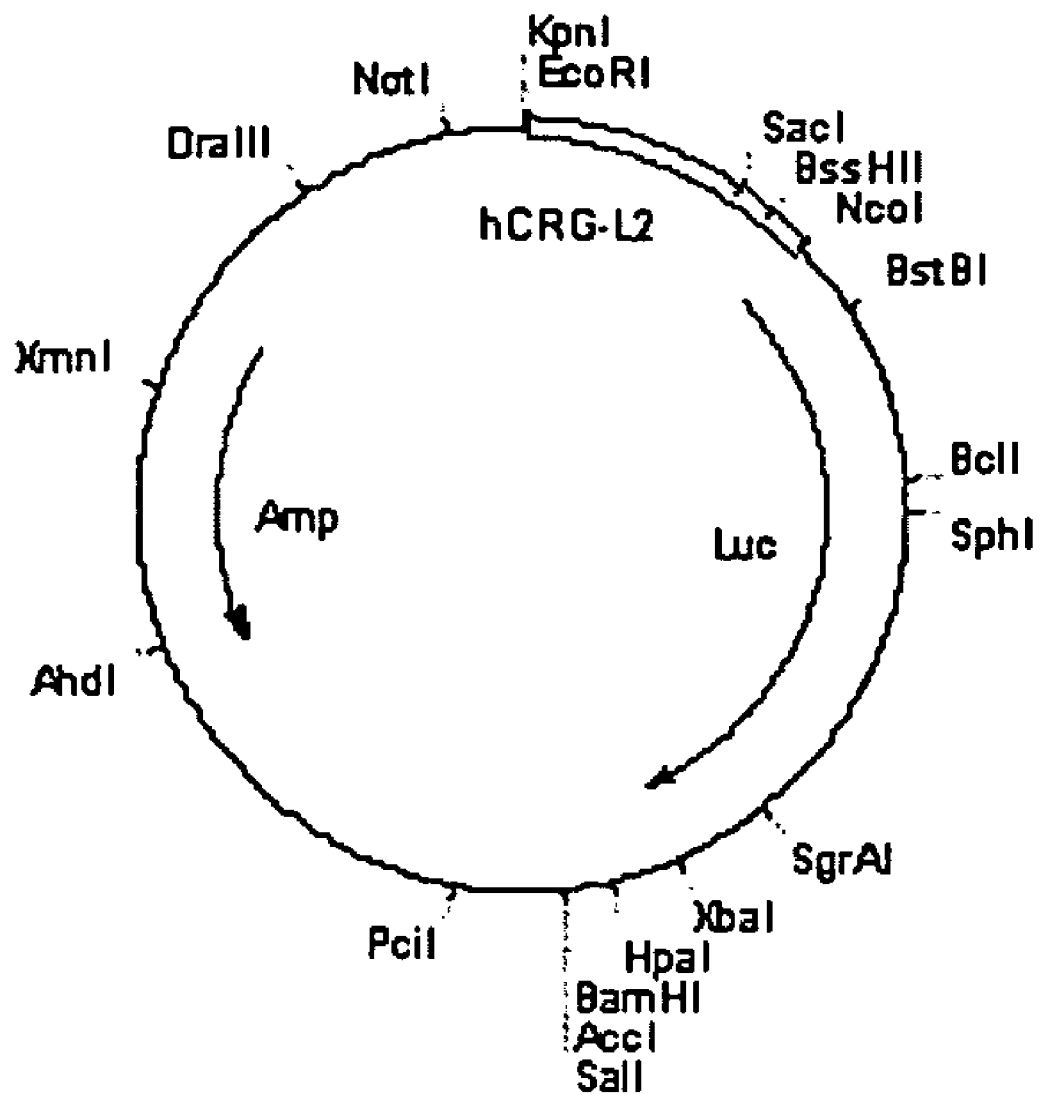
FIG. 2. CP1505 luciferase reporter construct containing the CRG-L2 0.7 Kb TRE DNA sequence.

The hepatocellular carcinoma-specific replication-competent adenovirus vectors of the invention comprise an adenovirus gene essential for replication, preferably an early gene, under the transcriptional control of a liver cancer-specific transcriptional regulatory element (TRE), preferably a CRG-L2 regulatory sequence. By providing one or more liver cancer-specific TREs, the adenovirus vectors effect selective replication and corresponding cytotoxicity in primary liver cancer cells.

The adenoviral vector comprising a liver cancer-specific TRE may further comprise one or more regulatory sequences, e.g. enhancers, promoters, transcription factor binding sites and the like, which may be derived from the same or different genes. The adenovirus vectors may comprise co-transcribed first and second genes under control of a liver cancer-specific TRE, wherein the second gene may be under translational control of an internal ribosome entry site (IRES). In some cases, the adenovirus vectors comprise more than two co-transcribed genes under control of a liver cancer-specific TRE, wherein one or more genes is under translational control of an internal ribosome entry site (IRES). The adenovirus vectors of the invention may or may not comprise the adenoviral E3 gene, an E3 sequence, or a portion thereof.

In another aspect, methods are provided for conferring selective cytotoxicity in target primary liver cancer cells, particularly hepatocellular carcinoma cells, comprising contacting the cells with an adenovirus vector of the invention, whereby the vector enters the cell and propagates virus. The replication of virus in primary liver cancer cells, as compared to non-tumor cells, or to normal, i.e. non-transformed cells, is usually about 10 fold greater, and may be about 100 fold greater, and in some instances is as much as about 1000 fold or more greater. The administration of virus may be combined with additional treatment(s) appropriate to the particular disease, e.g. antiviral therapy, chemotherapy, surgery, radiation therapy or immunotherapy. In some embodiments, this treatment suppresses tumor growth, e.g. by killing tumor cells. In other embodiments, the size and/or extent of a tumor is reduced, or its development delayed. Cytotoxicity is a term well understood in the art and refers to a state in which a cell's usual biochemical or biological activities are compromised (i.e., inhibited), including cell death and/or cytolysis. These activities include, but are not limited to, metabolism; cellular replication; DNA replication; transcription; translation; uptake of molecules. Assays known in the art as indicators of cytotoxicity, include dye exclusion, $^3$H-thymidine uptake, and plaque assays.

Individuals suitable for treatment by these methods include individuals who have or are suspected of having liver cancer, particularly hepatocellular carcinoma, including individuals in the early or late stages of the disease, as well as individuals who have previously been treated (e.g., are in the adjuvant setting). Other individuals suitable for the methods described herein are those who are considered high risk for developing liver cancer, such as those who are positive for infection with a hepatitis virus, which may include hepatitis B virus; and hepatitis C virus; individuals suffering from cirrhosis; etc. Treatment regimes include both the eradication of tumors or other forms of the disease, antiviral treatment, supportive treatment for liver function, as well as palliation of the disease. The presence of primary liver cancer and the suitability of the individual for receiving the methods described herein may be determined by any of the techniques known in the art, including diagnostic methods such as imaging techniques, analysis of serum tumor markers, and biopsy.

The invention provides novel regulatory sequences that provide for enhanced expression in hepatocellular carcinoma cells, set forth in SEQ ID NO:1. This region of DNA contains the native promoter elements that direct expression of the linked CRG-L2 gene.

The various methods of the invention will be described below. Although particular methods of tumor suppression are exemplified in the discussion below, it is understood that any of a number of alternative methods, including those described above are equally applicable and suitable for use in practicing the invention. It will also be understood that an evaluation of the vectors and methods of the invention may be carried out using procedures standard in the art, including the diagnostic and assessment methods described above.

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning:

A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Feigner and Ringold (1989) *Nature* 337:387-388; Berkner and Sharp (1983) *Nucl. Acids Res.* 11:6003-6020; Graham (1984) *EMBO J.* 3:2917-2922; Bett et al. (1993) *J. Virology* 67:5911-5921; Bett et al. (1994) *Proc. Natl. Acad. Sci. USA* 91:8802-8806.

Definitions

Unless otherwise indicated, all terms used herein have the same meaning as they would to one skilled in the art and the practice of the present invention will employ, conventional techniques of microbiology and recombinant DNA technology, which are within the knowledge of those of skill of the art.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

Hepatocellular carcinoma is a tumor that is relatively uncommon in the United States, although its incidence is rising, principally in relation to the spread of hepatitis C infection. It is the most common cancer in some other parts of the world, with more than one million new cases diagnosed each year. Hepatocellular carcinoma is potentially curable by surgical resection, but only for the small fraction of patients with localized disease. Prognosis depends on the degree of local tumor replacement and the extent of liver function impairment. Therapy other than surgical resection is often experimental in nature, including systemic or infusional chemotherapy, hepatic artery ligation or embolization, percutaneous ethanol injection, radiofrequency ablation, cryotherapy, and radiolabeled antibodies, often in conjunction with surgical resection and/or radiation therapy. A few patients may be candidates for liver transplantation, but the limited availability of livers for transplantation restricts the use of this approach. Hepatocellular carcinoma can coexist with bile duct cancer (cholangiocarcinoma).

Hepatocellular carcinoma is associated with cirrhosis in 50% to 80% of patients; 5% of cirrhotic patients eventually develop hepatocellular cancer, which is often multifocal. Hepatitis B infection and hepatitis C infection are the most significant causes of hepatocellular carcinoma worldwide, particularly in patients with continuing antigenemia and in those who have chronic active hepatitis. Aflatoxin has also been implicated as a factor in the etiology of primary liver cancer in parts of the world where this mycotoxin occurs in high levels in ingested food. Workers who were exposed to vinyl chloride before controls on vinyl chloride dust were instituted developed sarcomas in the liver, most commonly angiosarcomas.

The primary symptoms of hepatocellular carcinoma are those of a hepatic mass. Among patients with underlying cirrhotic disease, a progressive increase in alpha-fetoprotein (AFP) and/or in alkaline phosphatase or a rapid deterioration of hepatic function may be the only clue to the presence of the neoplasm. Infrequently, patients with this disease have polycythemia, hypoglycemia, hypercalcemia, or dysfibrinogenemia.

The biologic marker AFP is useful for the diagnosis of this neoplasm. By a radioimmunoassay technique, 50% to 70% of patients in the United States who have hepatocellular carcinoma have elevated levels of AFP. AFP levels have been shown to be prognostically important, with the median survival of AFP-negative patients significantly longer than that of AFP-positive patients. Other prognostic variables include performance status, liver functions, and the presence or absence of cirrhosis and its severity in relation to the Child-Pugh classification.

As used herein, "suppressing tumor growth" refers to reducing the rate of growth of a tumor, halting tumor growth completely, causing a regression in the size of an existing tumor, eradicating an existing tumor and/or preventing the occurrence of additional tumors upon treatment with the compositions, kits or methods of the present invention. "Suppressing" tumor growth indicates a growth state that is curtailed when compared to growth without contact with, i.e., transfection by, an adenoviral vector combined with administration of chemotherapeutic agents and radiation as described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

"Delaying development" of a tumor means to defer, hinder, slow, retard, stabilize, and/or postpone development of the disease. This delay can be of varying lengths of time, depending on the history of the disease and/or individual being treated.

As used herein, a "transcription response element" or "transcriptional regulatory element", or "TRE" is a polynucleotide sequence, preferably a DNA sequence, comprising one or more enhancer(s) and/or promoter(s) and/or promoter elements such as a transcriptional regulatory protein response sequence or sequences, which increases transcription of an operably linked polynucleotide sequence in a host cell that allows that TRE to function. A "hepatocellular carcinoma-specific transcriptional response element" preferentially directs gene expression in hepatocellular carcinoma cells. "Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

In addition to the hepatocellular carcinoma specific TRE, the vectors of the invention may further comprise promoters and/or enhancers derived from the same or different genes. Such additional regulatory elements may be operably linked to adenovirus genes essential for replication.

The term "composite TRE" refers to a TRE that comprises transcriptional regulatory elements that are not naturally found together, usually providing a non-native combination of promoters and enhancer, for example, a heterologous combination of promoter and enhancer and/or transcription factor binding sites; a combination of human and mouse promoter and enhancer; two or more enhancers in combination with a promoter; multimers of the foregoing; and the like. At least one of the promoter, enhancer or and/or transcription factor binding site elements will be hepatocellular carcinoma specific, for example the CRG-L2 promoter in combination with an enhancer. In other embodiments, two or more of the elements will provide hepatocellular carcinoma specificity. A composite TRE comprising regulatory elements from two or more sources may be used to regulate one or more adenovirus genes.

Alternatively, separate TREs may be operably linked to different adenoviral genes. For example, one TRE may regulate transcription of an adenovirus E1A gene, while a different TRE regulates expression of an adenovirus E1B gene. Additional TREs may also be operably linked to therapeutic sequences targeted for expression.

Without limitation, regulatory elements of interest for use in the present vectors may include the E2F promoter, the telomerase promoter, the H19 promoter (Brannan et al., Mol. and Cell. Biol., 10(1) 28-36, 1990; U.S. Pat. Nos. 5,955,273; 6,306,833), and the AFP promoter. Also of interest are promoter elements reported to be modified in HCC, including the promoters for cyclin-dependent kinase inhibitor 4a; caspase 8, apoptosis-related cysteine protease; ras association (RalGDS/AF-6) domain family 1 protein isoform 1 a; and cadherin 13, H-cadherin (see Yu et al. (2002) *BMC Cancer* 2:29).

By "transcriptional activation" or an "increase in transcription," it is intended that transcription is increased above basal levels in a normal, i.e. non-transformed cell by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-target cell (i.e., a different cell type), or the level of activity (if any) of a reporter construct lacking a hepatocellular carcinoma-specific TRE as tested in a target cell line. When the TRE controls a gene necessary for viral replication, the replication of virus is significantly higher in the target cells, as compared to a control cell, usually at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 100-fold higher, most preferably at least about $1 \times 10^6$ higher. Most preferably, the adenovirus replicates solely in the target cells (that is, does not replicate or replicates at a very low levels in non-target cells).

Activity of a TRE can be determined, for example, as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase (encoded by the lacZ gene), luciferase (encoded by the luc gene), alkaline phosphatase (AP), green fluorescent protein (GFP), and horseradish peroxidase (HRP). Such vectors and assays are readily available, from, inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes, DEAE dextran-mediated transfer, particle bombardment or direct injection. TRE activity is measured by detection and/or quantitation of reporter gene-derived mRNA and/or protein. Reporter protein product can be detected directly (e.g., immunochemically) or through its enzymatic activity, if any, using an appropriate substrate. Generally, to determine cell specific activity of a TRE, a TRE-reporter gene construct is introduced into a variety of cell types. The amount of TRE activity is determined in each cell type and compared to that of a reporter gene construct lacking the TRE. A TRE is determined to be cell-specific if it is preferentially functional in one cell type, compared to a different type of cell.

A hepatocellular carcinoma specific TRE comprises a mammalian hepatocellular carcinoma-specific enhancer and/or promoter. Preferred metastatic cancer-specific enhancers and/or promoters for use in practicing the invention are of human, rat or mouse origin, including promoter and enhancer elements and transcription factor binding sequences from the 5' CRG-L2 sequence set forth in SEQ ID NO:1. In one embodiment, the TRE comprises SEQ ID NO:1, residues 119-803. Transcriptional regulatory sequences of interest known to confer specificity include the promoter and enhancer elements from CRG-L2 as described herein. This region of DNA contains the native promoter elements that direct expression of the linked gene. Usually a promoter region will have at least about 100 nt of sequence located 5' to the gene and further comprising a TATA box and CAAT box motif sequence.

The sequence of this 5' region, and further 5' upstream sequences may be utilized to direct gene expression, including enhancer binding sites, that provide for expression in tissues where CRG-L2 is expressed, e.g. hepatocellular carcinoma cells. The tissue specific expression is useful for determining the pattern of expression, and for providing promoters that mimic the native pattern of expression. Sequence alterations, including substitutions, deletions and additions, may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc.

The regulatory sequences may be used to identify cis acting sequences required for transcriptional or translational regulation of CRG-L2 expression, especially in different stages of metastasis, and to identify cis acting sequences and trans acting factors that regulate or mediate expression. Such transcription or translational control regions may be operably linked to a gene of interest in order to promote expression of a protein of interest in cultured cells, or in embryonic, fetal or adult tissues, and for gene therapy.

A hepatocellular carcinoma-specific TRE can also comprise multimers. For example, a hepatocellular carcinoma-specific TRE can comprise a tandem series of at least two, at least three, at least four, or at least five promoter fragments. Alternatively, a hepatocellular carcinoma-specific TRE could have one or more promoter regions along with one or more enhancer regions. These multimers may also contain heterologous promoter and/or enhancer sequences and/or transcription factor binding sites.

The promoter enhancer and/or transcription factor binding site components of a hepatocellular carcinoma-specific TRE may be in any orientation and/or distance from the coding sequence of interest, as long as the desired target cell-specific transcriptional activity is obtained. Transcriptional activation can be measured in a number of ways known in the art, but is generally measured by detection and/or quantitation of mRNA or the protein product of the coding sequence under control of (i.e., operably linked to) the hepatocellular carcinoma-specific TRE. As discussed herein, a hepatocellular carcinoma-specific TRE can be of varying lengths, and of varying sequence composition.

As is known in the art, the activity of TREs can be inducible. Inducible TREs generally exhibit low activity in the absence of inducer, and are up-regulated in the presence of inducer. Inducers include, for example, nucleic acids, polypeptides, small molecules, organic compounds and/or environmental conditions such as temperature, pressure or hypoxia. Inducible TREs may be preferred when expression is desired only at certain times or at certain locations, or when it is desirable to titrate the level of expression using an inducing agent.

A TRE for use in the present vectors may or may not comprise a silencer. The presence of a silencer (i.e., a negative regulatory element known in the art) can assist in shutting off transcription (and thus replication) in non-target cells. Thus, the presence of a silencer can confer enhanced cell-specific vector replication by more effectively preventing replication in non-target cells. Alternatively, the lack of a silencer may stimulate replication in target cells, thus conferring enhanced target cell-specificity.

A "functionally-preserved variant" of a hepatocellular carcinoma-specific TRE differs, usually in sequence, but still retains the biological activity, e.g., target cell-specific transcription activity of the corresponding native or parent hepatocellular carcinoma-specific TRE, although the degree of activation may be altered. The difference in sequence may arise from, for example, single base mutation(s), addition(s), deletion(s), and/or modification(s) of the bases. The difference can also arise from changes in the sugar(s), and/or linkage(s) between the bases of a hepatocellular carcinoma-specific TRE. For example, certain point mutations within sequences of TREs have been shown to decrease transcription factor binding and stimulation of transcription (see Blackwood, et al. (1998) Science 281:60-63, and Smith et al. (1997) J. Biol. Chem. 272:27493-27496). One of skill in the art would recognize that some alterations of bases in and around transcription factor binding sites are more likely to negatively affect stimulation of transcription and cell-specificity, while alterations in bases that are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription. It will be appreciated that typically a "functionally-preserved variant" of a hepatocellular carcinoma-specific TRE will hybridize to the parent sequence under conditions of high stringency. Exemplary high stringency conditions include hybridization at about 65° C. in about 5×SSPE and washing at about 65° C. in about 0.1×SSPE (where 1×SSPE=0.15 sodium chloride, 0.010 M sodium phosphate, and 0.001 M disodium EDTA). Further examples of high stringency conditions are provided in: Maniatis, et al., MOLECULAR CLONING: A LABORATORY MANUAL, 2d Edition (1989); and Ausubel, F. M., et al., Eds., CURRENT PROTOCOLS IN MOLECULAR BIOLOGY, John Wiley & Sons, Inc., Copyright (c)1987, 1988, 1989, 1990 by Current Protocols, both of which are hereby incorporated by reference.

In some instances, a "functionally-preserved variant" of a hepatocellular carcinoma-specific TRE is a fragment of a native or parent hepatocellular carcinoma-specific TRE. The term "fragment," when referring to a hepatocellular carcinoma-specific TRE, refers to a sequence that is the same as part of, but not all of, the nucleic acid sequence of a native or parental hepatocellular carcinoma-specific TRE. Such a fragment either exhibits essentially the same biological function or activity as the native or parental hepatocellular carcinoma-specific TRE; for example, a fragment which retains the target cell-specific transcription activity of the corresponding native or parent hepatocellular carcinoma-specific TRE, although the degree of activation may be altered.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene (Jackson et al. (1990) *Trends Biochem Sci* 15(12):477-83) and Jackson et al. (1995) *RNA* 1(10):985-1000). The present invention encompasses the use of any IRES element that is able to direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, *Trends Biochem Sci* 15(12):477-483); and IRES obtainable from viral or cellular mRNA sources, such as for example, immunoglobulin heavy-chain binding protein (BiP), the vascular endothelial growth factor (VEGF) (Huez et al. (1998) *Mol Cell. Biol.* 18(11):6178-6190), the fibroblast growth factor 2, and insulin-like growth factor, the translational initiation factor eIF4G, yeast transcription factors TFIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, the term "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) *J. Virol* 66(3):1602-1609). In another illustrative embodiment disclosed herein, the IRES is from VEGF. In some embodiments, an adenovirus vector comprising an IRES and a target cell-specific TRE exhibits greater specificity for the target cell than an adenovirus vector comprising a target cell-specific TRE and lacking an IRES.

In some embodiments, specificity is conferred by preferential transcription and/or translation of the first and second genes due to the presence of a target cell specific TRE. In other embodiments, specificity is conferred by preferential replication of the adenovirus vectors in target cells due to the target cell-specific TRE driving transcription of a gene essential for replication.

An "E3 region" (used interchangeably with "E3") is a term well understood in the art and means the region of the adenoviral genome that encodes the E3 gene products. Generally, the E3 region is located between about nucleotides 28583 and 30470 of the adenoviral genome. The E3 region has been described in various publications, including, for example, Wold et al. (1995) *Curr. Topics Microbiol. Immunol.* 199:237-274. A "portion" of the E3 region means less than the entire E3 region, and as such includes polynucleotide deletions as well as polynucleotides encoding one or more polypeptide products of the E3 region.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of a single transcriptional control element.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector. Any vector for use in gene introduction can basically be used as a "vector" into which the DNA having promoter activity is to be introduced. Particularly in gene therapy, viral vectors, such as retrovirus vectors, adenovirus vectors, or adeno associated virus vectors, and non-viral vectors such as liposomes should be used. Plasmid vectors may also find use. Any cell is included in the "cell carrying the expression vector" of the present invention.

The term "plasmid" as used herein refers to a DNA molecule that is capable of autonomous replication within a host cell, either extrachromosomally or as part of the host cell chromosome(s). The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeable with plasmids described herein.

Methods that are well known to those skilled in the art can be used to construct expression vectors containing coding sequences and appropriate transcriptional and translational control signals, including a liver cancer specific control signal, for specific expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In mammalian host cells, a number of viral-based expression systems may be utilized, including retroviral vectors (e.g. derived from MoMLV, MSCV, SFFV, MPSV, SNV etc), lentiviral vectors (e.g. derived from HIV-1, HIV-2, SIV, BIV, FIV etc.), adeno-associated virus (MV) vectors, adenoviral vectors (e.g. derived from Ad5 virus), SV40-based vectors, Herpes Simplex Virus (HSV)-based vectors etc. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Nati. Acad. Sci. USA 81:3655-3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-™ expression system from Clontech (Clontechniques (January 2000) p. 10-12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

An "adenovirus vector" or "adenoviral vector" (used interchangeably) of the invention is a polynucleotide construct, which is replication competent, exhibits preferential replication in primary liver cancercells and contains a tissue-specific transcriptional regulatory sequence linked to an adenoviral gene. In some embodiments, an adenoviral vector of the invention includes a therapeutic gene sequence, e.g., a cytokine gene sequence. Exemplary adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. Preferably, an adenoviral polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes for inclusion in the adenovirus vectors of the invention, are provided below.

In the context of adenovirus, a "heterologous" promoter or enhancer is one which is not associated with or derived from an adenovirus gene.

In the context of a target cell-specific TRE, a "heterologous" promoter or enhancer is one which is derived from a gene other than the gene from which a particular target cell-specific TRE is derived.

In the context of adenovirus, an "endogenous" promoter, enhancer, or TRE is native to or derived from adenovirus.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a virus yield assay, burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

"Preferential replication" and "selective replication" may be used interchangeably and mean that an adenovirus replicates more in a target cell than in a non-target cell. Preferably, the adenovirus replicates at a significantly higher rate in target cells than non target cells; preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates only in the target cells (that is, does not replicate at all or replicates at a very low level in non-target cells).

An "individual" is a vertebrate, preferably a mammal, more preferably a human. Mammals include, but are not limited to, farm animals, sport animals, rodents, primates, and pets. A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the invention on a cell which allows or induces a target cell-specific TRE to function (referred to herein as a "target cell") when compared to the cytotoxicity conferred by an adenoviral vector of the present invention on a cell which does not allow a target cell-specific TRE to function (a "non-target cell"). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

Adenoviral Vectors

The adenoviral vectors used in the methods described herein are replication-competent liver cancer-specific adenoviral vectors comprising an adenovirus gene, preferably a gene essential for replication under transcriptional control of a hepatocellular carcinoma-specific TRE. The vector may or may not include an E3 region. In other embodiments, an adenovirus vector is a replication competent liver cancer-specific vector comprising E1B, wherein E1B has a deletion of part or all of the 19-kDa region. In some embodiments the adenoviral gene essential for replication is an early gene, preferably E1A or E1B or both. In some embodiments, the adenovirus vector comprises co-transcribed first and second genes under transcriptional control of a heterologous, liver cancer-specific transcriptional regulatory element (TRE), wherein the second gene is under translational control of an internal ribosome entry site (IRES). The adenovirus vector may further comprise E3.

The E1B 19-kDa region refers to the genomic region of the adenovirus E1B gene encoding the E1B 19-kDa product. According to wild-type Ad5, the E1B 19-kDa region is a 261 bp region located between nucleotide 1714 and nucleotide 2244. The E1B 19-kDa region has been described in, for example, Rao et al., *Proc. Natl. Acad. Sci. USA,* 89:7742-7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19kDa.

The adenovirus vectors used in this invention replicate preferentially in hepatocellular carcinoma cells, which replication preference is indicated by comparing the level of replication (i.e., titer) in hepatocellular carcinoma cells to the level of replication in non-hepatpcellular carcinoma cells, normal or control cells. Comparison of the adenovirus titer of a hepatocellular carcinoma cell to the titer of a TRE inactive cell type provides a key indication that the overall replication preference is enhanced due to the replication in target cells as well as depressed replication in non-target cells. This is especially useful in the metastatic cancer context, in which targeted cell killing is desirable. Runaway infection is prevented due to the cell-specific requirements for viral replication. Without wishing to be bound by any particular theory, production of adenovirus proteins can serve to activate and/or stimulate the immune system, either generally or specifically toward target cells producing adenoviral proteins which can be an important consideration in the cancer context, where individuals are often moderately to severely immunocompromised.

In one aspect of the present invention, the adenovirus vectors comprise an intergenic IRES element(s) which links the translation of two or more genes, thereby removing any potential for homologous recombination based on the presence of identical TREs in the vector. Adenovirus vectors comprising an IRES are stable and in some embodiments provide better specificity than vectors not containing an IRES. Another advantage of an adenovirus vector comprising an intergenic IRES is that the use of an IRES rather than a second TRE may provide additional space in the vector for an additional gene(s) such as a therapeutic gene. Accordingly, in one aspect of the invention, the viral vectors disclosed herein typically comprise at least one IRES within a multicistronic transcript, wherein production of the multicistronic transcript is regulated by a heterologous, target cell-specific TRE. For adenovirus vectors comprising a second gene under control of an IRES, it is preferred that the endogenous promoter of the gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and the second gene are in frame. Alternatively, if the IRES does not contain an initiation codon or if the initiation codon is removed from the IRES, the initiation codon of the second gene is used. In one embodiment, the adenovirus vectors comprise the adenovirus essential genes, E1A and E1B genes, under the transcriptional control of a heterologous hepatocellular carcinoma-specific TRE, and an IRES introduced between E1A and E1B. Thus, both E1A and E1B are under common transcriptional control, and translation of E1B coding region is obtained by virtue of the presence of the IRES. In one embodiment, E1A has its endogenous promoter deleted. In another embodiment, E1A has an endogenous enhancer deleted and in yet an additional embodiment, E1A has its endogenous promoter deleted and E1A enhancer deleted. In another embodiment, E1B has its endogenous promoter deleted. In yet further embodiments, E1B has a deletion of part or all of the 19-kDa region of E1B.

An adenovirus vector may further include an additional heterologous TRE which may or may not be operably linked to the same gene(s) as the target cell-specific TRE. For example a TRE (such as a cell type-specific or cell status-specific TRE) may be juxtaposed to a second type of target-cell-specific TRE. "Juxtaposed" means a target cell-specific TRE and a second TRE transcriptionally control the same gene. For these embodiments, the target cell-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene.

To provide cytotoxicity to target cells, one or more transgenes having a cytotoxic effect may be present in the vector. Additionally, or alternatively, an adenovirus gene that contributes to cytotoxicity and/or cell death, such as the adenovirus death protein (ADP) gene, can be included in the vector, optionally under the selective transcriptional control of a heterologous TRE and optionally under the translational control of an IRES.

In some embodiments, an adenovirus vector of the invention comprises a transgene, which may confer a therapeutic effect, such as enhancing cytotoxicity so as to eliminate unwanted target cells. The transgene may be under the transcriptional control of a hepatocellular carcinoma TRE, e.g. a CRG-L2 TRE, which may comprise a CRG-L2 promoter. The transgene may be regulated independently of the adenovirus gene regulation, i.e. having separate promoters, which may the same or different, or may be coordinately regulated, i.e. having a single promoter in conjunction with an IRES.

In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the target cell-specific cytotoxic activity with cell-specific expression of, for example, HSV-tk which and/or cytosine deaminase (cd). Cancer cells can be induced to be conditionally sensitive to the antiviral drug ganciclovir after transduction with HSV-tk. Ganciclovir is converted by HSV-tk into its triphosphate form by cellular enzymes and incorporated into the DNA of replicating mammalian cells leading to inhibition of DNA replication and cell death. Cytosine deaminase renders cells capable of metabolizing 5-fluorocytosine (5-FC) to the chemotherapeutic agent 5-flurouracil (5-FU).

Other desirable transgenes that may be introduced via an adenovirus vector(s) include genes encoding cytokines such as interferons and interleukins; genes encoding lymphokines; genes coding for membrane receptors such as the receptors recognized by pathogenic organisms (viruses, bacteria or parasites), preferably by the HIV virus (human immunodeficiency virus); genes coding for coagulation factors such as factor VIII and factor IX; genes coding for dystrophins; genes coding for insulin; genes coding for proteins participating directly or indirectly in cellular ion channels, such as the CFTR (cystic fibrosis transmembrane conductance regulator) protein; genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene; genes coding for a protein inhibiting an enzyme activity, such as α1-antitrypsin or a viral protease inhibitor, for example; genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV; genes coding for antigenic epitopes in order to increase the host cell's immunity; genes coding for major histocompatibility complex classes I and II proteins, as well as the genes coding for the proteins which are inducers of these genes; genes coding for antibodies; genes coding for immunotoxins; genes encoding toxins; genes encoding growth factors or growth hormones; genes encoding cell receptors and their ligands; genes encoding tumor suppressors; genes coding for cellular enzymes or those produced by pathogenic organisms; and suicide genes.

Cytotoxic genes of interest include the A chains of diphtheria toxin, ricin or abrin (Palmiter et al. (1987) *Cell* 50: 435; Maxwell et al. (1987) *Mol. Cell. Biol* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *MoL Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. pepsin, papain, proteinase K, carboxypeptidase, etc.), or encode the Fas gene, and the like.

The HSV-1 TK suicide gene may be mentioned as an example. This viral TK enzyme displays markedly greater affinity compared to the cellular TK enzyme for certain nucleoside analogues (such as acyclovir or gancyclovir). It converts them to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

Although any gene or coding sequence of therapeutic relevance can be used in the practice of the invention, certain genes, or fragments thereof, are particularly suitable. For example, genes encoding immunogenic polypeptides, toxins, immunotoxins and cytokines are useful in the practice of the invention. Cytokine genes of use in the invention include, but are not limited to, those encoding α, β or γ interferon (IFN), interleukins (IL) such as IL-2, IL-6, IL-10 or IL-12, tumor necrosis factor (TNF), livery stimulating factors such as GM-CSF, C-CSF, M-CSF, and other cytokines as are known to those of skill in the art. Additional genes include those encoding cell or nuclear receptors and their ligands (e.g., fas ligand), coagulation factors (for example, FVIII, FIX), growth hormones, growth factors such as fibroblast growth factors (FGF), vascular endothelial growth factors (VEGF), nerve growth factors (NGF), epidermal growth factors (EGF), platelet-derived growth factors (PDGF) and other growth factors as are known to those of skill in the art. Genes suitable for use in the practice of the invention can encode enzymes (such as, for example, urease, renin, thrombin, metalloproteases, nitric oxide synthase, superoxide dismutase, catalase and others known to those of skill in the art), enzyme inhibitors (such as, for example, α1-antitrypsin, antithrombin III, cellular or viral protease inhibitors, plasminogen activator inhibitor-1, tissue inhibitor of metalloproteases, etc.), the cystic fibrosis transmembrane conductance regulator (CFTR) protein, insulin, dystrophin, or a Major Histocompatibility Complex (MHC) antigen of class I or II. Also useful are genes encoding polypeptides that can modulate/regulate expression of corresponding genes, polypeptides capable of inhibiting a bacterial, parasitic or viral infection or its development (for example, antigenic polypeptides, antigenic epitopes, and transdominant protein variants inhibiting the action of a native protein by competition), apoptosis inducers or inhibitors (for example, Bax, Bc12, Bc1X and others known to those of skill in the art), cytostatic agents (e.g., p21, p16, Rb, etc.), apolipoproteins (e.g., ApoAI, ApoAIV, ApoE, etc.), angiogenesis inhibitors (e.g., angiostatin, endostatin, etc.), oxygen radical scavengers, polypeptides having an anti-tumor effect, antibodies, toxins, immunotoxins, markers (e.g., β-galactosidase, luciferase, etc.) or any other genes of interest that are recognized in the art as being useful for treatment or prevention of a clinical condition.

Suitable genes of interest to delay or inhibit tumor or cancer progression, include but are not limited to those encoding an antisense RNA, a ribozyme, a cytotoxic product such as thymidine kinase of herpes simplex virus type 1 (HSV-1 TK), ricin, a bacterial toxin, the products of the yeast genes FCY1 and/or FUR1 having CDase (cytosine deaminase) and UPRTase (uracil phosphoribosyl transferase) activities respectively, an antibody, a polypeptide inhibiting cellular division or signal transduction, a tumor suppressor gene (such as, for example, p53, Rb, p73), a polypeptide which activates the host immune system, a tumor-associated antigen (e.g., MUC-1, BRCA-1, an HPV early or late antigen such as E6, E7, L1, L2, etc), optionally in combination with a cytokine gene.

Functionally preserved variants of TREs can be used in the vectors disclosed herein. Variant TREs retain function in the target cell but need not exhibit maximal function. In fact, maximal transcriptional activation activity of a TRE may not always be necessary to achieve a desired result, and the level of induction afforded by a fragment of a TRE may be sufficient for certain applications. For example, if used for treatment or palliation of a disease state, less-than-maximal responsiveness may be sufficient if, for example, the target cells are not especially virulent and/or the extent of disease is relatively confined.

As discussed herein, a TRE can be of varying lengths, and of varying sequence composition. The size of a heterologous TRE will be determined in part by the capacity of the viral vector, which in turn depends upon the contemplated form of the vector (see infra). Generally minimal sizes are preferred for TREs, as this provides potential room for insertion of other sequences which may be desirable, such as transgenes, and/or additional regulatory sequences. In a preferred embodiment, such an additional regulatory sequence is an IRES. However, if no additional sequences are contemplated, or if, for example, an adenoviral vector will be maintained and delivered free of any viral packaging constraints, larger TRE sequences can be used as long as the resultant adenoviral vector remains replication-competent.

To minimize non-specific replication, endogenous adenovirus TREs are preferably removed from the vector. Besides facilitating target cell-specific replication, removal of endogenous TREs also provides greater insert capacity in a vector, which may be of special concern if an adenoviral vector is to be packaged within a virus particle. Even more importantly, deletion of endogenous TREs prevents the possibility of a recombination event whereby a heterologous TRE is deleted and the endogenous TRE assumes transcriptional control of its respective adenovirus coding sequences. However, endogenous TREs can be maintained in the adenovirus vector(s), provided that sufficient cell-specific replication preference is preserved. These embodiments are constructed by inserting heterologous TREs between an endogenous TRE and a replication gene coding segment. Requisite liver cancer-specific replication preference is determined by conducting assays that compare replication of the adenovirus vector in a cell which allows function of the heterologous TREs with replication in a cell which does not.

The adenovirus vectors of this invention can be prepared using recombinant techniques that are standard in the art. Generally, a liver cancer-specific TRE is inserted 5' to the adenoviral gene of interest, preferably an adenoviral replication gene, more preferably one or more early replication genes (although late gene(s) can be used). A hepatocellular carcinoma-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for a hepatocellular carcinoma-specific TRE. Accordingly, convenient restriction sites for annealing (i.e., inserting) a hepatocellular carcinoma-specific TRE can be engineered onto the 5' and 3' ends of a UP-TRE using standard recombinant methods, such as PCR.

Adenoviral vectors containing all replication-essential elements, with the desired elements (e.g., E1A) under control of a liver cancer-specific TRE, are conveniently prepared by homologous recombination or in vitro ligation of two plasmids, one providing the left-hand portion of adenovirus and the other plasmid providing the right-hand region, one or more of which contains at least one adenovirus gene under control of a hepatocellular carcinoma-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from a hepatocellular carcinoma-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003-6020; Bridge et al. (1989) *J. Virol* 63: 631-638.

For convenience, plasmids are available that provide the necessary portions of adenovirus. Plasmid pXC.1 (McKinnon (1982) *Gene* 19:3342) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb TRE without deleting the endogenous enhancer/promoter. The gene for E3 is located on the opposite strand from E4 (r-strand). pBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of a liver cancer-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of a hepatocellular carcinoma-specific TRE at that site.

A similar strategy may also be used for insertion of a liver cancer-specific TRE element to regulate E1B. The E1B promoter of Ad5 consists of a single high-affinity recognition site for SpI and a TATA box. This region extends from Ad5 nt 1636 to 1701. By insertion of a TRE in this region, one can provide for cell-specific transcription of the E1B gene. By employing the left-hand region modified with the cell-specific response element regulating E1A, as the template for introducing a liver cancer-specific TRE to regulate E1B, the resulting adenovirus vector will be dependent upon the cell-specific transcription factors for expression of both E1A and E1B. In some embodiments, part or all of the 19-kDa region of E1B is deleted.

Similarly, a liver cancer-specific TRE can be inserted upstream of the E2 gene to make its expression cell-specific. The E2 early promoter, mapping in Ad5 from 27050-27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Micro. and Immunol* (1995) 199(part 3):177-194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of a hepatocellular carcinoma-specific TRE having SpeI ends into the SpeI site in the 1-strand would disrupt the endogenous E2 early promoter of Ad5 and should allow cell-restricted expression of E2 transcripts.

For E4, one must use the right hand portion of the adenovirus genome. The E4 transcription start site is predominantly at about nt 35605, the TATA box at about nt 35631 and the first AUG/CUG of ORF I is at about nt 35532. Virtanen et al. (1984) *J. Virol.* 51: 822-831. Using any of the above strategies for the other genes, a UP-TRE may be introduced upstream from the transcription start site. For the construction of full-length adenovirus with a hepatocellular carcinoma-specific TRE inserted in the E4 region, the co-transfection and homologous recombination are performed in W162 cells (Weinberg et al. (1983) *Proc. Natl. Acad. Sci.* 80:5383-5386) which provide E4 proteins in trans to complement defects in synthesis of these proteins.

Adenoviral constructs containing an E3 region can be generated wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Insertion of an IRES into a vector is accomplished by methods and techniques that are known in the art and described herein supra, including but not limited to, restriction enzyme digestion, ligation, and PCR. A DNA copy of an IRES can be obtained by chemical synthesis, or by making a cDNA copy of, for example, a picornavirus IRES. See, for example, Duke et al. (1995) *J. Virol.* 66(3):1602-9) for a description of the EMCV IRES and Huez et al. (1998), *Mol. Cell. Biol.* 18(11):6178-90) for a description of the VEGF IRES. The internal translation initiation sequence is inserted into a vector genome at a site such that it lies upstream of a 5' -distal coding region in a multicistronic mRNA. For example, in a preferred embodiment of an adenovirus vector in which production of a bicistronic E1A-E1B mRNA is under the control of a liver cancer-specific TRE, the E1B promoter is deleted or inactivated, and an IRES sequence is placed between E1A and E1B. In other embodiments, part or all of the 19-kDa region of E1B is deleted. IRES sequences of cardioviruses and certain aphthoviruses contain an AUG codon at the 3' end of the IRES that serves as both a ribosome entry site and as a translation initiation site. Accordingly, this type of IRES is introduced into a vector so as to replace the translation initiation codon of the protein whose translation it regulates. However, in an IRES of the entero/rhinovirus class, the AUG at the 3' end of the IRES is used for ribosome entry only, and translation is initiated at the next downstream AUG codon. Accordingly, if an entero/rhinovirus IRES is used in a vector for translational regulation of a downstream coding region, the AUG (or other translation initiation codon) of the downstream gene is retained in the vector construct.

Methods of packaging polynucleotides into adenovirus particles are known in the art and are also described in co-owned PCT PCT/US98/04080.

Therapeutic Methods

An effective amount of the adenovirus vector is administered to a patient as a composition in a pharmaceutically acceptable excipient (and may or may not be in the same compositions), including, but not limited to, saline solutions, suitable buffers, preservatives, stabilizers, and may be administered in conjunction with suitable agents such as antiemetics. An effective amount is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state. Some individuals are refractory to these treatments, and it is understood that the methods encompass administration to these individuals. The amount to be given will be determined by the condition of the individual, the extent of disease, the route of administration, how many doses will be administered, and the desired objective.

Delivery of adenoviral vectors is generally accomplished by either site-specific injection or intravenous injection. Site-specific injections of vector may include, for example, injections into liver lesions, as well as intraperitoneal, intrapleural, intrathecal, intra-arterial, intra-tumor injections or topical application. These methods are easily accommodated in treatments using the combination of adenoviral vectors and chemotherapeutic agents.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo).

If used as a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 μg to about 1000 μg of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, or by employing a technique such as an immunoadsorption procedure (e.g., immunoapheresis) that removes adenovirus antibody from the blood, so as to permit repetitive administration, without a strong immune response. If packaged as another viral form, such as HSV, an amount to be administered is based on standard knowledge about that particular virus (which is readily obtainable from, for example, published literature) and can be determined empirically.

Embodiments of the present invention include methods for the administration of combinations of a liver cancer-specific adenoviral vector and a second anti-neoplastic therapy, which may include radiation, an anti-neoplastic agent, etc., to an individual with neoplasia, as detailed in co-owned U.S. application Ser. No. 09/814,357, expressly incorporated by reference herein. The chemotherapeutic agent and adenovirus may be administered simultaneously or sequentially, with various time intervals for sequential administration. In some embodiments, an effective amount of an adenoviral vector and an effective amount of at least one antineoplastic agent are combined with a suitable excipient and/or buffer solutions and administered simultaneously from the same solution by any of the methods listed herein or those known in the art. This may be applicable when the antineoplastic agent does not compromise the viability and/or activity of the adenoviral vector itself.

Where more than one antineoplastic agent is administered, the agents may be administered together in the same composition; sequentially in any order; or, alternatively, administered simultaneously in different compositions. If the agents are administered sequentially, administration may further comprise a time delay. Sequential administration may be in any order, and accordingly encompasses the administration of an effective amount of an adenoviral vector first, followed by the administration of an effective amount of the chemotherapeutic agent. The interval between administration of adenovirus and chemotherapeutic agent may be in terms of at least (or, alternatively, less than) minutes, hours, or days. Sequential administration also encompasses administration of a chosen antineoplastic agent followed by the administration of the adenoviral vector. The interval between administration may be in terms of at least (or, alternatively, less than) minutes, hours, or days.

Administration of the above-described methods may also include repeat doses or courses of target-cell specific adenovirus and chemotherapeutic agent depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth. A particular course of treatment according to the above-described methods, for example, combined adenoviral and chemotherapy, may later be followed by a course of combined radiation and adenoviral therapy.

Anti-neoplastic agents include those from each of the major classes of chemotherapeutics, including but not limited to: alkylating agents, alkaloids, antimetabolites, anti-tumor antibiotics, nitrosoureas, hormonal agonists/antagonists and analogs, immunomodulators, photosensitizers, enzymes and others. In some embodiments, the antineoplastic is an alkaloid, an antimetabolite, an antibiotic or an alkylating agent. In certain embodiments the antineoplastic agents include, for example, thiotepa, interferon alpha-2a, and the M-VAC combination (methotrexate-vinblastine, doxorubicin, cyclophosphamide). Preferred antineoplastic agents include, for example, 5-fluorouracil, cisplatin, 5-azacytidine, and gemcitabine. Particularly preferred embodiments include, but are not limited to, 5-fluorouracil gemcitabine, doxorubicin, miroxantrone, mitomycin, dacarbazine, carmustine, vinblastine, lomustine, tamoxifen, docetaxel, paclitaxel or cisplatin. The specific choice of both the chemotherapeutic agent(s) is dependent upon, inter alia, the characteristics of the disease to be treated. These characteristics include, but are not limited to, location of the tumor, stage of the disease and the individual's response to previous treatments, if any.

In addition to the use of single antineoplastic agents in combination with a particular adenoviral vector, the invention also includes the use of more than one agent in conjunction with an adenoviral vector. These combinations of antineoplastics when used to treat neoplasia are often referred to as combination chemotherapy and are often part of a combined modality treatment which may also include surgery and/or radiation, depending on the characteristics of an individual's cancer. It is contemplated that the combined adenoviral/chemotherapy of the present invention can also be used as part of a combined modality treatment program.

There are a variety of delivery methods for the administration of antineoplastic agents, which are well known in the art, including oral and parenteral methods. There are a number of drawbacks to oral administration for a large number of antineoplastic agents, including low bioavailability, irritation of the digestive tract and the necessity of remembering to administer complicated combinations of drugs. The majority of parenteral administration of antineoplastic agents is intravenously, as intramuscular and subcutaneous injection often leads to irritation or damage to the tissue. Regional variations of parenteral injections include intra-arterial, intravesical, intra-tumor, intrathecal, intrapieural, intraperitoneal and intracavity injections.

Delivery methods for chemotherapeutic agents include intravenous, intraparenteral and introperitoneal methods as well as oral administration. Intravenous methods also include delivery through a vein of the extremities as well as including more site specific delivery, such as an intravenous drip into the portal vein of the liver. Other intraparenteral methods of delivery include direct injections of an antineoplastic solution, for example, subcutaneously, intracavity or intra-tumor.

Assessment of the efficacy of a particular treatment regimen may be determined by any of the techniques known in the art, including diagnostic methods such as imaging techniques, analysis of serum tumor markers, biopsy, the presence, absence or amelioration of tumor associated symptoms. It will be understood that a given treatment regime may be modified, as appropriate, to maximize efficacy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The following examples are offered by way of illustration and not by way of limitation.

Experimental

Using a hepatocellular carcinoma (HCC) mouse model, it has been shown that the CRG-L2 gene is specifically expressed in the HCC tissue, but not normal liver tissue. In this model, in situ hybridization showed that CRG-L2 mRNA levels increased during early development of HCC (see Graveel et al. (2003) Oncogene 22:1730-1736). In humans, CRG-L2 mRNA is upregulated in HCC tissues but displays restricted expression in normal tissues, except for the placenta. Based on this discovery, CGI initiated a research collaboration to clone the CRG-L2 TRE.

Figure 3:
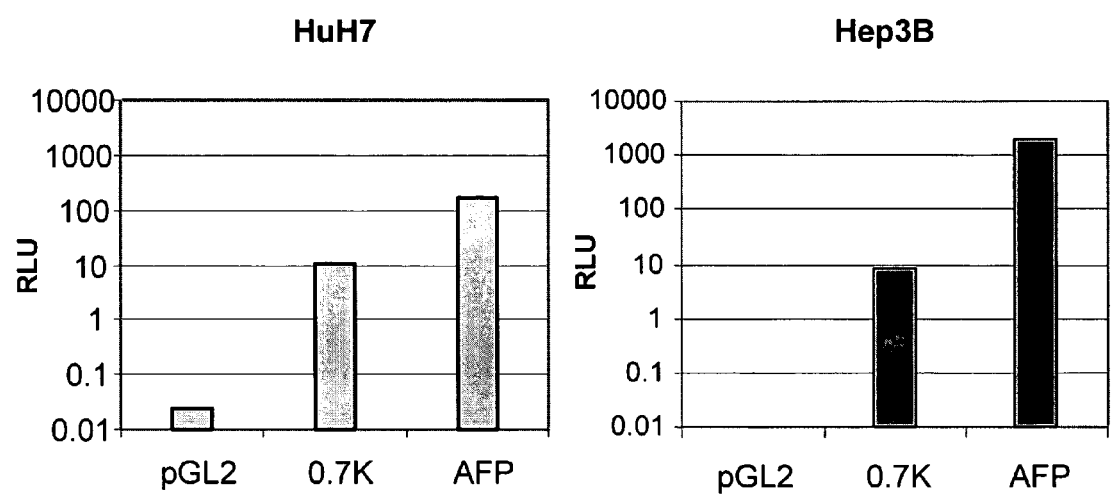
FIG. 3. Reporter gene assay to evaluate promoter activity in hepatoma cells. CRG-L2 promoter activity in Hep3B and HuH7 HCC cell lines is ≧100 fold higher than pGL2 negative control. Since both cell lines are AFP positive, AFP promoter was used as a positive control.
Figure 4:
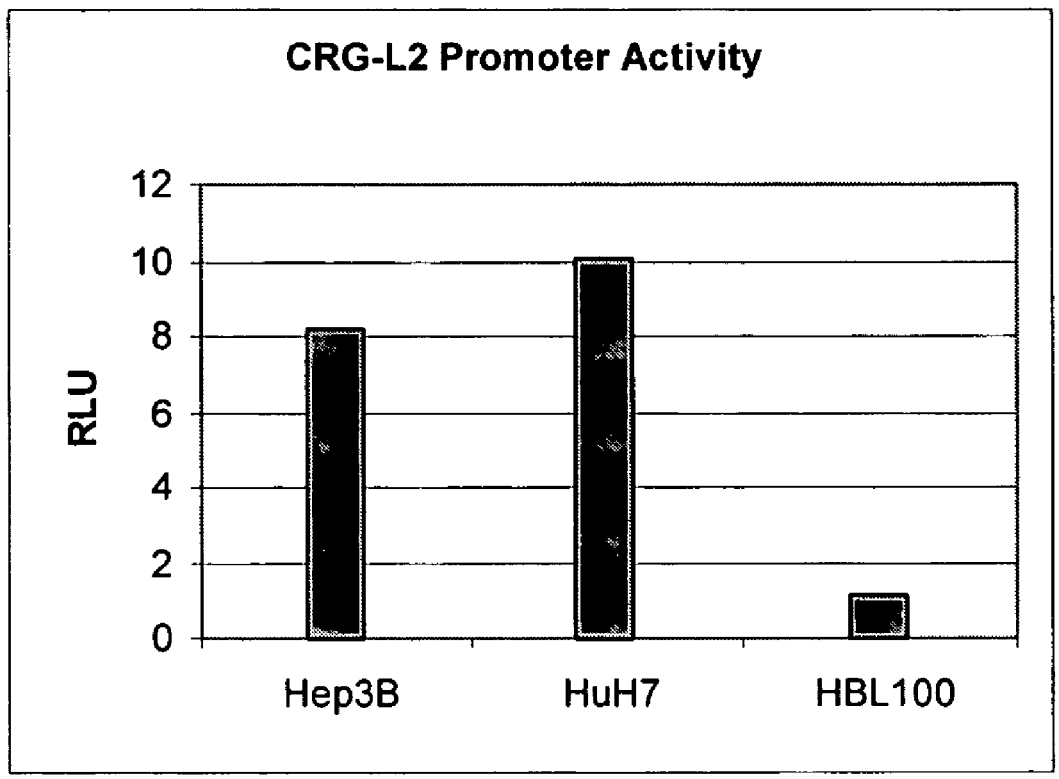
FIG. 4: CRG-L2 promoter expression in Hep3B, HuH7 and HBL-100 cells. The expression of CRG-L2 in HBL-100 cells is 8-10 fold less than that in Hep3B and HuH7 cells, suggesting cell specificity.

In order to characterize the CRG-L2 transcriptional regulatory elements, a series of cloned DNA fragments upstream of the CRG-L2 gene were analyzed. A 0.7 kb DNA fragment from the upstream region of the CRG-L2 gene was shown to have promoter activity in HCC cell lines (FIG. 1). The construct CP1505 (CRG-L2 0.7 kb), pGL2 (promoter-less luciferase construct), and AFP luciferase construct were transfected into Hep3B and HuH7 cells. After 72 hours, cells were harvested and assayed for luciferase activity. Data presented in FIG. 3 showed that both Hep3B and HuH7 cells transfected with CP1505 produced a significant luciferase activity. In contrast, the luciferase activity detected in HBL-100 cells (FIG. 4) is eight to ten fold less than the activity seen in Hep3B and HuH7 cells, demonstrating cell specificity.

It is evident from the above results that adenoviruses can be developed with specificity for particular host cells, where the viruses are replication-competent. The viruses may be vehicles for the introduction of a wide variety of genes into particular target cells.

The invention now being fully described, it will be apparent to one of ordinary skill in the art that many changes and modifications can be made thereto without departing from the spirit or scope of the appended claims.

provides for expression of the adenovirus gene essential for replication in hepatocellular carcinoma cells expressing CRG-L2.

2. The adenovirus vector according to claim 1, wherein said CRG-L2 TRE comprises a human promoter or enhancer.

3. The adenovirus vector according to claim 1 further comprising a second human transcriptional regulatory element.

4. The adenovirus vector according to claim 1, wherein said hepatocellular carcinoma cell specific TRE comprises two or more enhancers.

5. The adenovirus vector according to claim 1, wherein the adenoviral vector further comprises a second adenovirus gene co-transcribed under transcriptional control of the TRE.

6. The adenovirus vector according to claim 5, wherein the second adenovirus gene is under translational control of an IRES.

7. The adenovirus vector of claim 1, wherein said adenoviral gene essential for replication is E1A or E1B.

8. The adenovirus vector of claim 7, wherein E1A or E1B has a mutation in or deletion of its endogenous promoter.

What is claimed is:

1. A replication-competent adenovirus vector comprising an adenovirus gene essential for replication under transcriptional control of a hepatocellular carcinoma specific TRE, wherein said TRE consists essentially of a CRG-L2 TRE selected from the group consisting of SEQ ID NO: 1 and nucleotides 119-803 of SEQ ID NO: 1, and wherein the TRE 9. The adenovirus vector of claim 7, wherein the E 1B gene's 19-kDa region is deleted.

10. A composition comprising:
   the replication-competent adenovirus vector according to claim 1 and a pharmaceutically acceptable excipient.

11. A host cell line comprising the adenovirus vector of claim 1.

* * * * *

```
                        SEQUENCE LISTING

<160> NUMBER OF SEQ ID NOS: 1

<210> SEQ ID NO 1
<211> LENGTH: 803
<212> TYPE: DNA
<213> ORGANISM: Homo sapiens

<400> SEQUENCE: 1
acctcccatg  dacagtgggc  acgtgcctta  gcatctgggc  atgctgatct  ttttctccaa    60
gagggcagtg  tgggggtaga  aggggdtgga  atccggagac  ttctctccat  aagaattcct   120
gctctccccc  tcagtctgac  ccttgctttg  cctgtctggg  ccacggcaat  gccctcaggc   180
agagcagtgg  gaagaggagg  agagggtttg  ctcagctggc  gggactctgg  gagcacgagc   240
cctgccagcc  cctcctccgc  aggctgcctc  cactggctcc  tctcctgctt  ctgcccgcct   300
gtccctctgg  gctgctcggg  cgccaccact  actgtcccca  tcccgccccg  ccagctgggc   360
caaagggtga  cttgactcac  gacgctgcca  ccagcccacg  gcttgcccga  ggcgtataaa   420
ggctgccagg  gccgcaggct  gccaagccct  gccctgccca  aggcgcatag  agcatggccc   480
gaggcgctga  gggaggccgt  ggggacgcgg  gttgggggcct  gcgtggcgcc  ctggcggccg   540
tggcgctgct  ctcggcgctc  aacgctgcgg  gcacggtgtt  cgcgctgtgc  cagtggcgcg   600
ggctgagctc  ggcgctgcgg  gctttggagg  cgcagcgggg  ccgggagcag  cgcgaggaca   660
gtgccctgcg  ctccttcctg  gccgagttga  gccgcgcgcc  gcgcggggcg  tccgcaccac   720
cccaagaccc  ggccagctca  gctcgcaaca  agcgcagcca  cagcggcgag  cccgcgccgc   780
atatccgcgc  cgagagccat  gac                                              803
```